(12) United States Patent
Braach-Maksvytis et al.

(10) Patent No.: US 6,348,319 B1
(45) Date of Patent: Feb. 19, 2002

(54) ENZYME DETECTION BIOSENSORS

(75) Inventors: Vijoleta Lucija Bronislava Braach-Maksvytis, Dulwich Hills; Bruce Andrew Cornell, Neutral Bay; David Geoffrey Thomson, Narara; Burkhard Raguse, St. Ives, all of (AU)

(73) Assignees: Australian Membrane and Biotechnology Research Institute, New South Wales; University of Sydney, Sydney, both of (AU)

( * ) Notice: Subject to any disclaimer, the term of this patent is extended or adjusted under 35 U.S.C. 154(b) by 0 days.

(21) Appl. No.: 09/125,068

(22) PCT Filed: Feb. 10, 1997

(86) PCT No.: PCT/AU97/00071

§ 371 Date: Nov. 10, 1998

§ 102(e) Date: Nov. 10, 1998

(87) PCT Pub. No.: WO97/29366

PCT Pub. Date: Aug. 14, 1997

Related U.S. Application Data

(60) Provisional application No. 60/011,314, filed on Feb. 8, 1996.

(51) Int. Cl.[7] ............................................. G01N 33/573
(52) U.S. Cl. .................... 435/7.1; 204/400; 204/403; 204/418; 422/82.01; 422/82.02; 435/7.4; 435/287.1; 435/287.2; 435/817; 436/149; 436/528; 436/806

(58) Field of Search ................................. 204/400, 403, 204/418; 422/82.01, 82.02; 435/7.4, 7.1, 287.1, 287.2, 817; 436/528, 149, 806

(56) References Cited

U.S. PATENT DOCUMENTS

| | | | |
|---|---|---|---|
| 5,204,239 A | * | 4/1993 | Gitler et al. .................. 435/7.1 |
| 5,234,566 A | * | 8/1993 | Osman et al. ............... 204/403 |
| 5,286,365 A | * | 2/1994 | Shu ............................... 204/418 |
| 5,328,847 A | * | 7/1994 | Case et al. .................... 435/817 |
| 5,368,712 A | * | 11/1994 | Tomich et al. .............. 204/403 |
| 5,401,378 A | * | 3/1995 | King et al. .................. 204/418 |
| 5,436,170 A | * | 7/1995 | Cornell et al. .............. 436/527 |
| 5,591,647 A | * | 1/1997 | King ............................ 436/518 |
| 5,693,477 A | * | 12/1997 | Cornell et al. ............... 435/7.1 |
| 5,766,960 A | * | 6/1998 | Cornell et al. .............. 436/501 |

* cited by examiner

*Primary Examiner*—Christopher L. Chin
(74) *Attorney, Agent, or Firm*—Nixon & Vanderhye (57) ABSTRACT

The present invention provides a biosensor for use in detecting the presence of an enzyme or enzymes in a sample. The biosensor comprises a membrane and means for determining the impedance of the membrane. The membrane includes ionophores therein to which are attached linkers. The linkers are cleavable by the enzyme or enzymes to be detected, with the cleavage of the linker causing a change in the ability of ions to pass through the membrane via the ionophores.

27 Claims, 10 Drawing Sheets

Fig. 7 GDPE

Fig. 8 DPE-PC

SEQUENCE LISTING

<160> NUMBER OF SEQ ID NOS: 4

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence:cholera
      toxin probe

<400> SEQUENCE: 1
ctccggagca tagagcttgg agg                                          23

<210> SEQ ID NO 2
<211> LENGTH: 15
<212> TYPE: DNA
<213> ORGANISM: Artificial Sequence
<220> FEATURE:
<223> OTHER INFORMATION: Description of Artificial Sequence:non-specific
      binding probe

<400> SEQUENCE: 2
attgctacgt atacg                                                   15

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence:listeria
      probe

<400> SEQUENCE: 3
atagttttat gggattagc                                               19

-continued

```
<210> SEQ ID NO 4
<211> LENGTH: 52
<212> TYPE: DNA
<213> ORGANISM: Artificial Sequence
<220> FEATURE:
<223> OTHER INFORMATION: Description of Artificial Sequence:5', 19 base
      listeria sequence, 10 base spacer, 23 base cholera toxin sequence

<400> SEQUENCE: 4
gctaatccca taaaactatg catgcatatc ctccaagctc tatgctccgg ag           52
```

ENZYME DETECTION BIOSENSORS

This application claims benefit to Provisional Application No. 60/011,314 filed Feb. 8, 1996.

The present invention relates to biosensors and methods involving the use of these biosensors in detecting the presence of enzymes by detecting their enzymatic activity.

BACKGROUND OF THE INVENTION

A number of proteins which are useful as immunodiagnostic analytes and disease markers have the additional property of enzymatic activity, in particular protease activity. In addition, other classes of proteins exhihibit nuclease activity.

Prostate Specific Antigen (PSA), a diagnostic marker for prostate cancer is an example of a protein which exhibits protease activity, and belongs to the class of proteins known as the serine proteases. Examples of other proteases which are important immunodiagnostic markers include blood coagulation enzymes, elastase, cathepsin B.

There are also a number of important industrial enzymes such as subtilisin, papain and α-amylase.

Examples of important nucleases are restriction enzymes, e.g., BamH1. Hind III, polymerases which can act as nucleases under certain conditions. e.g., T4 DNA polymerase, reverse transcriptase, which acts as an Rnase under certain conditions, e.g. Rnase H, and exo- and endo-nucleases, e.g. S1 nuclease.

Current diagnostic tests employ immunoassays for the detection of PSA (e.g. a number of analytical instruments such as Abbott's AXsym. Boehringer Mannheim's Elecsys, and CIBA-Corning's ACS-180. all have ELISA-based PSA tests). These tests use antibodies raised against the PSA molecule which recognise the specific epitope sites within the protein molecule.

A variation on these approaches is disclosed in International Patent application No. PCT/AU95/00536. In this reference there is disclosed a range of substrates specifically cleaved by PSA. There is also disclosure in this reference of an assay system for proteases such as PSA which make use of the activity of the protease. This assay system involves the use of a ligand to capture the PSA and the subsequent use of a substrate for the PSA.

SUMMARY OF THE INVENTION

The present inventors have developed devices and methods for the detection of enzymes which make use of the protein's protease activity. These devices and methods involve the use of membrane based biosensors. Information regarding such biosensors can be found in International Patent Application Nos PCT/AU88/00273, PCT/AU89/00352, PCT/AU90/00025, PCT/AU92/00132, PCT/AU93/00509, PCT/AU93/00620, PCT/AU94/00202 and PCT/AU95/00763. The disclosure of each of these applications is included herein by reference.

The present invention involves providing a substrate for the enzyme to be detected and then sensing the digestion of the substrate by the enzyme. This may be achieved in a number of ways, for example the digestion of the substrate may remove a group from the ionophore thereby releasing the ionophore so that it diffuses laterally within the membrane or may result in an increase in the ability of ions to pass through the ionophore simply by a reduction in "steric" hindrance. Alternatively the digestion of the substrate when attached to a membrane spanning component may result in the release of the ionophore such that it may diffuse laterally within the membrane Clearly this could also be achieved by digestion of substrates attached to both the ionophore and membrane spanning component.

In another arrangement the digestion of the substrate results in the release of ionophore including probe which then inserts itself into the membrane.

Accordingly, in a first aspect the present invention consists in a biosensor for use in detecting the presence of an enzyme in a sample, the biosensor comprising a membrane and means for determining the impedance of the membrane, the membrane having ionophores therein to which are attached linkers, the linkers being cleavable by the enzyme to be detected, the cleavage of the linker causing a change in the ability of ions to pass through the membrane via the ionophores.

In a preferred embodiment of the present invention the linker is attached to the membrane such that the ionophore is prevented from diffusing laterally within the membrane. It is preferred that the linker is attached to membrane spanning components provided in the membrane. This attachment may be achieved in a number of ways such as covalent attachment, however, it is presently preferred that the attachment is achieved by providing on each of the linker and membrane spanning component one member of a ligand binding pair. A preferred ligand binding pair is biotin streptavidin. In another preferred arrangement both the membrane spanning component and the linker are provided with moieties which are both bound to the same molecule, for example biotin is provided on both the membrane spanning component and the linker and there is cross-linking via streptavidin.

The moiety on the membrane spanning component may also be attached via a linker. This may be the same linker as that provided on the ionophore or may be different.

In a further preferred embodiment the membrane comprises a first and second layer of a closely packed array of amphiphilic molecules, a plurality of ionophores and a plurality of membrane-spanning lipids prevented from lateral diffusion in the membrane, the ionophores comprising first and second half membrane spanning monomers, the first half membrane spanning monomers being provided in the first layer and the second half membrane spanning monomers being provided in the second layer, the first half membrane spanning monomers being prevented from lateral diffusion in the first layer, the second half membrane spanning monomers being linked to the membrane spanning lipids via the linker. Following cleavage of the linker by the enzyme the second half membrane spanning monomers can diffuse laterally within the second layer independent of the first half membrane spanning monomers.

In a second aspect the present invention consists in a biosensor for use in detecting the presence of an enzyme in a sample, the biosensor comprising a membrane and means for determining the impedance of the membrane, the membrane having a plurality of ionophores and a plurality of membrane-spanning components therein, the membrane-spanning components having attached thereto linker molecules to which are connected the ionophores, the linker molecules being cleavable by the enzyme to be detected, the cleavage of the linker molecules causing a change in the ability of ions to pass through the membrane via the ionophores.

In a preferred embodiment the membrane comprises a first and second layer of a closely packed array of amphiphilic molecules and the membrane-spanning components are prevented from lateral diffusion in the membrane. Preferably the ioniophores comprise first and second half membrane spanning monomers, the first half membrane spanning monomers being provided in the first layer and the second half membrane spanning monomers being provided in the second layer with the first half membrane spanning monomers being prevented from lateral diffusion in the first layer. The second half membrane spanning monomers are connected to the membrane-spanning components via the linker molecule.

The ionophores in both these aspects are preferably gramicidin or analogues thereof.

While a range of enzymes can be detected using the biosensor or the present invention the biosensor is particularly useful in the detection of proteases, in particular those of clinical importance such as PSA, fibrinogen etc.

In a third aspect the present invention consists in a biosensor for the detection of enzymes comprising first and second zones, means to allow addition of a sample suspected to contain an enzyme to the first zone, the first zone containing a probe linked to a carrier via a linker cleavable by the enzyme and means to allow passage of unlinked probe from the first zone to the second zone; the second zone including a membrane the impedance of which is dependent on the presence or absence of the probe and means to measure the impedance of the membrane.

In a preferred embodiment of this aspect of the present invention the membrane comprises a first and a second layer of a closely packed array of amphiphilic molecules and a plurality of ionophores comprising a first and second half membrane spanning monomers, the first half membrane spanning monomers being provided in the first layer and the second half membrane spanning monomers being provided in the second layer. The second half membrane spanning monomers being capable of lateral diffusion within the second layer independent of the first half membrane spanning monomers, the first half membrane spanning monomers being prevented from lateral diffusion in the first layer, and a ligand provided on at least the second half membrane spanning monomers, said ligand being reactive with the probe or a portion thereof, the binding of the probe to the ligand causing a change in the relationship between the first half membrane spanning monomers and the second half membrane spanning monomers such that the flow of ions across the membrane via the ionophores is allowed or prevented.

In a preferred embodiment the probe includes streptavidin and the ligand includes biotin.

In yet another preferred embodiment the probe includes an ionophore such that when the probe comes into contact with the membrane the ionophore inserts itself into the membrane changing the impedance of the membrane, As an example of such an arrangement the probe may include valinomycin which inserts itself into the membrane.

In a preferred embodiment of the present invention the enzyme to be detected is a protease in particular Prostate Specific Antigen. In this case it is preferred that the linker or linker molecule includes the sequence Ala-Val-Tyr.

As will be recognised by those skilled in the art the actual linker used will depend on the enzyme to be detected. Examples of some enzymes and their corresponding substrates are set out in Whittaker et al. Analytical Biochemistry: 220, 238–243 (1994), the disclosure of which is incorporated by cross-reference.

In a further aspect the present invention consists in a method of detecting the presence of an enzyme in a sample comprising adding the sample to the biosensor of the first or second or third aspect of the present invention and measuring the change in impedance of the membrane.

As will be readily apparent the biosensors and methods of the present invention do not detect total enzyme: they detect only active enzyme. This is important as in a number of situations it is the amount of active enzyme present which is of importance not simply the total amount of enzyme present as would be measured in a standard sandwich ELISA.

It will also be apparent that the sensors of the present invention can be used to detect a wide range of enzymes. These enzymes include nucleases, protease amylases etc. The sensors are adapted to the particular enzyme to be detected by adjusting the make-up of the linker. For example to detect proteases the linker will typically include a peptide portion which is cleaved by the enzyme. Information regarding peptide sequences cleaved by specific proteases is provided in Whittaker et al referred to above, Where the enzyme to be detected is a nuclease the linker will typically include a nucleic acid sequence. Information regarding specific sequences cleaved by specific enzymes can be found in "Current Protocols in Molecular Biology" Ausebel et al (1987) John Wiley & Sons, N.Y.

The sensors of the present invention may also find use in drug development for determining DNA-drug binding sites. The sensors could also be used in determining DNA-protein binding sites. The sensors may also find use in diagnosing infection. For example the sensors could be used to detect enzyme activity specifically associated with a pathogen.

Industrially and clinically relevant proteases and substrates include thrombin and serine proteases including PSA. A list of lysis enzymes is found in "Specificity of Proteolysis" Borivoj Keil (1992) Springer Verlag N.Y. pp. 283–323. Useful ones are the serine and cysteine proteases. See also "Proteolytic Enzymes": a Practical Approach" R. J. Benyon & J. S. Bond (eds) 1989 Oxford University Press N.Y. p232, pp. 241–249. Commercially significant proteases and protease inhibitors for which the present technology is relevant are available in serine, cysteine, aspartic and metallo types. The serine proteases include the endoproteinase-Arg-C, -Glu-C, Lys-C, factor Xa, proteinase K. subtilisin and trypsin, and the exopeptidases acylamino-acid-releasing enzyme, carboxypeptidase P, and carboxypeptidase Y. The cysteine proteases include the endopeptidases bromelain, cathepsin B. clostripain, papain, and the exopeptidases cathepsin C and pyroglutamate aminopeptidase. The aspartic proteases include the endopeptidases cathepsin D and pepsin. The metallo proteases include the endopeptidase thermolysin and the exopeptidases aminopeptidase M, carboxypeptidase-A, -B and leucine aminopeptidase. The listing is not intended to be exclusive and indicates the broad utility of the present invention. Other commercially useful proteases are listed in the publications cited above, which are included herein by reference. For example it also includes the endopeptide endoproteinase-Asp-N of unknown type.

BRIEF DESCRIPTION OF THE DRAWINGS

In order that the nature of the present invention may be more clearly understood preferred forms thereof will now be described by reference to the following Examples and accompanying Figures, in which.

DETAILED DESCRIPTION OF PREFERRED EMBODIMENTS

Figure 1:
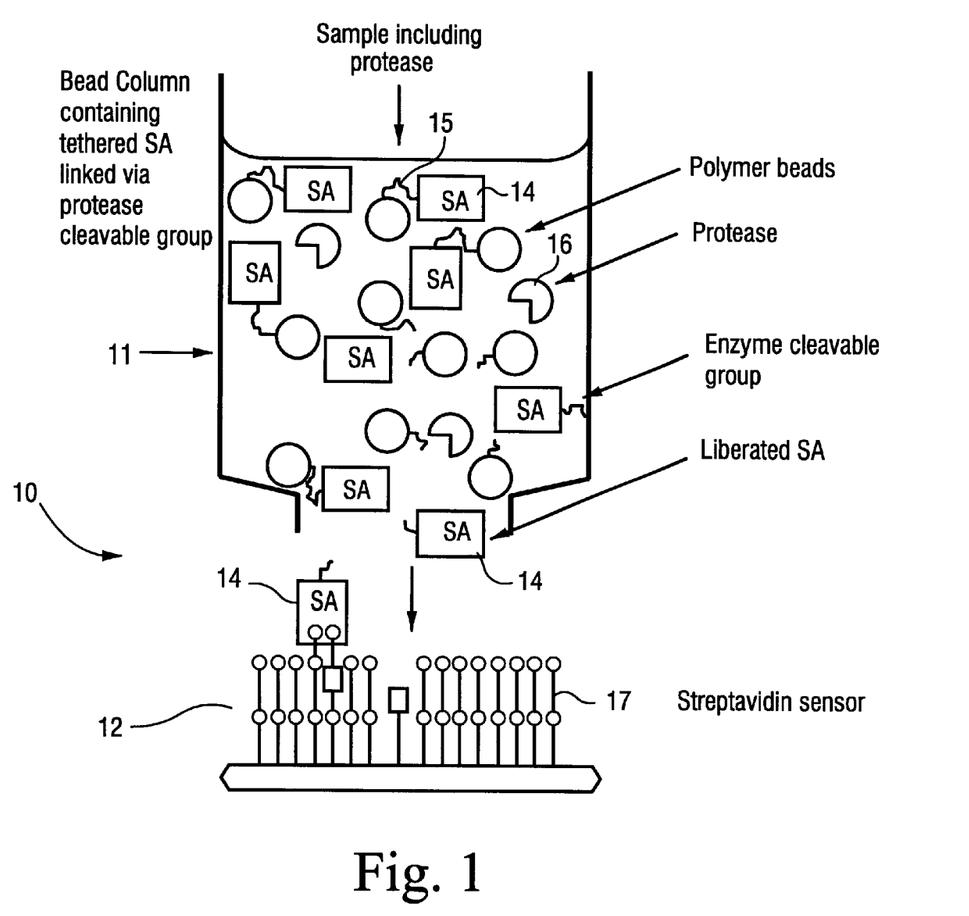
FIG. 1 is a schematic representation of an embodiment of the device of the third aspect of the present invention.

FIG. 1 shows a schematic representation of an embodiment of the device of the third aspect of the present invention. As can be seen from this Figure the device 10 includes a first zone 11 and a second zone 12. First zone 11 is provided with polymer beads 13 (carrier) linked to streptavidin 14 (probe) via a peptide linker 15. The peptide linker 15 is cleavable by the protease 16.

As shown in this Figure upon addition of the protease (or a nuclease) 16 the streptavidin 14 is released and passes to the second zone 12. Second zone 12 includes a biosensor membrane 17 which detects the presence of streptavidin 14. Streptavidin 14 reaching biosensor membrane 17 causes a change in the impedance of the membrane.

Figure 2:
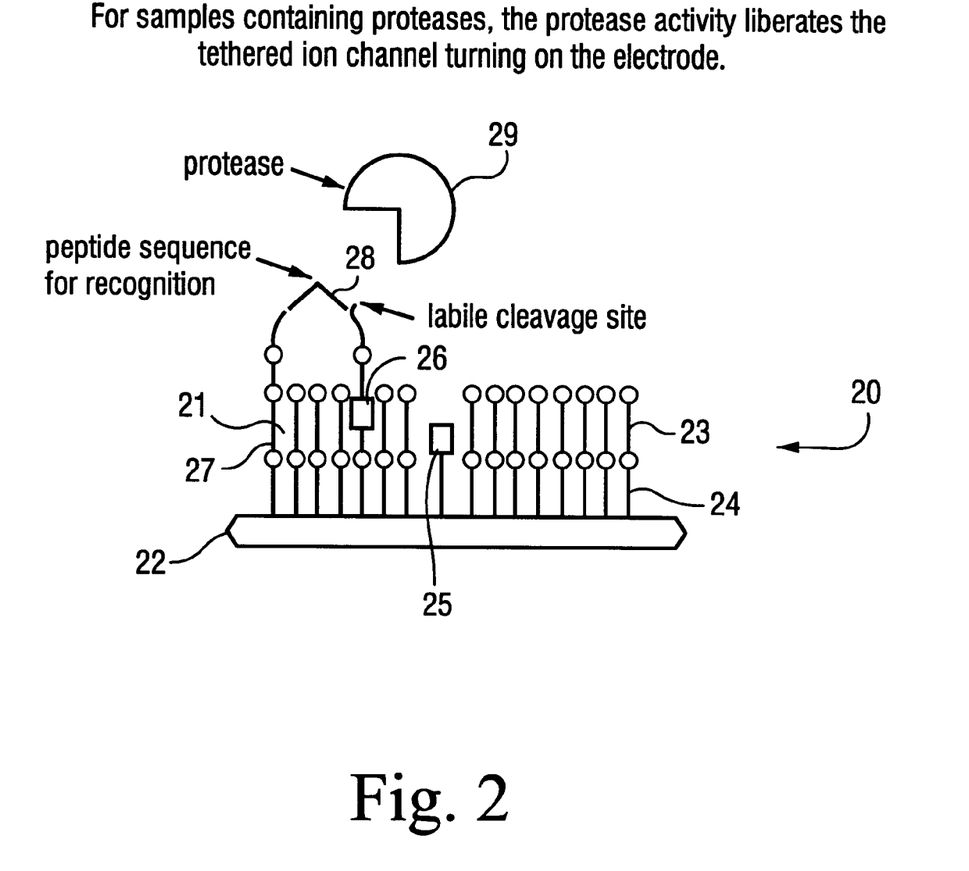
FIG. 2 shows an embodiment of the first and/or second aspect of the invention.

FIG. 2 shows an embodiment of the first and/or second aspect of the invention. As shown in FIG. 2 the biosensor membrane 20 includes a membrane 21 and eletrode 22. The membrane 21 has a first layer 23 and second layer 24 of arrays of amphiphilic molecules. Included in layer 24 is a first half membrane-spanning monomer 25 which is prevented from lateral diffusion within the membrane. Layer 23 includes a second half membrane-spanning monomer 26. The membrane also includes a membrane-spanning lipid 27 which is also prevented from diffusing laterally within the membrane. The second half membrane-spanning monomer 26 is linked to the membrane-spanning lipid 27 via a peptide 28. The peptide 28 is cleavable by protease 29. Upon cleavage of the peptide 28 by protease 29 the half membrane-spanning monomer 26 is free to diffuse laterally within the membrane. This results in a change in impedance of the membrane.

EXAMPLES

Example 1
Protease cleavage of streptavidin-gramicidin linkage

Figure 3:
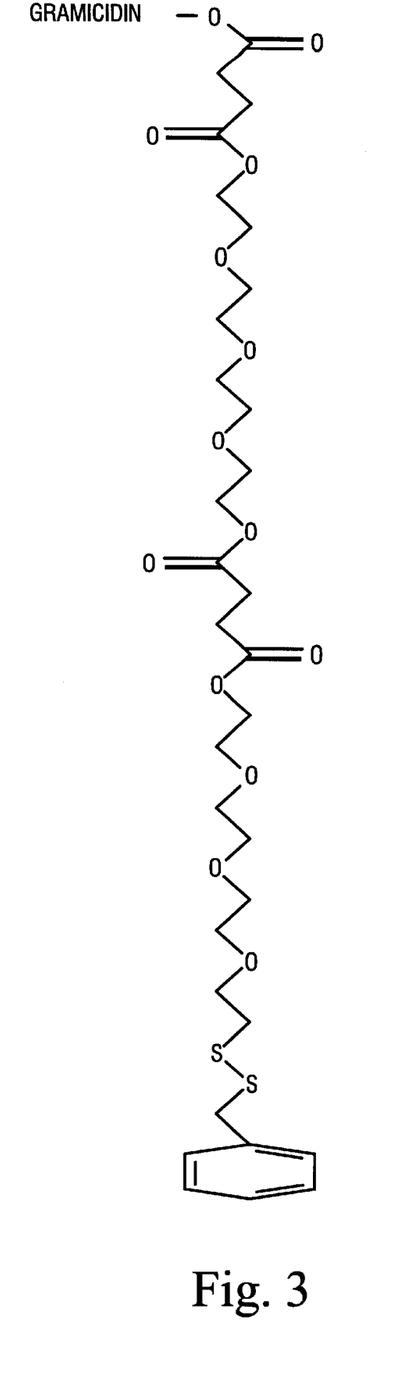
FIG. 3 is Gramicidin B.
Figure 4:
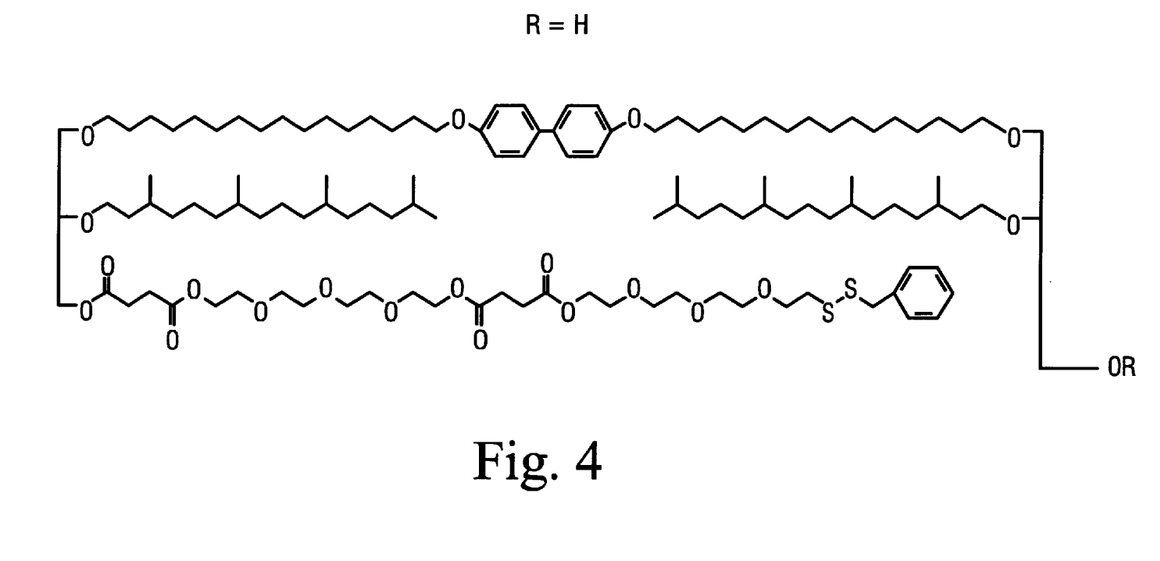
FIG. 4 is Spanner Lipid.
Figure 5:
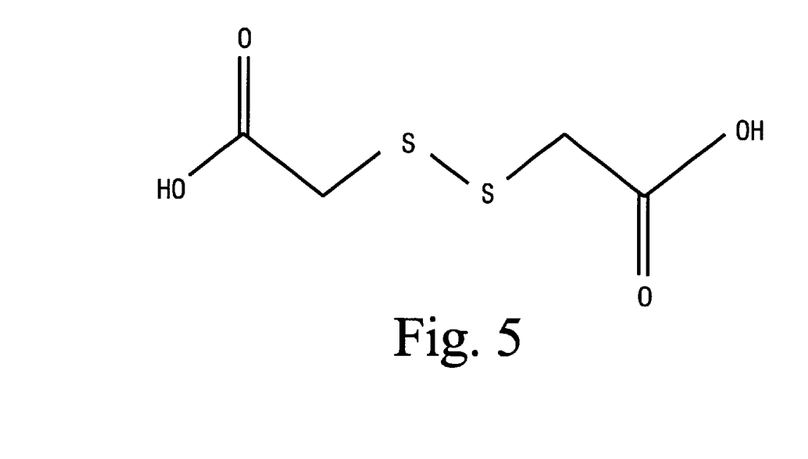
FIG. 5 is MAAD.
Figure 6:
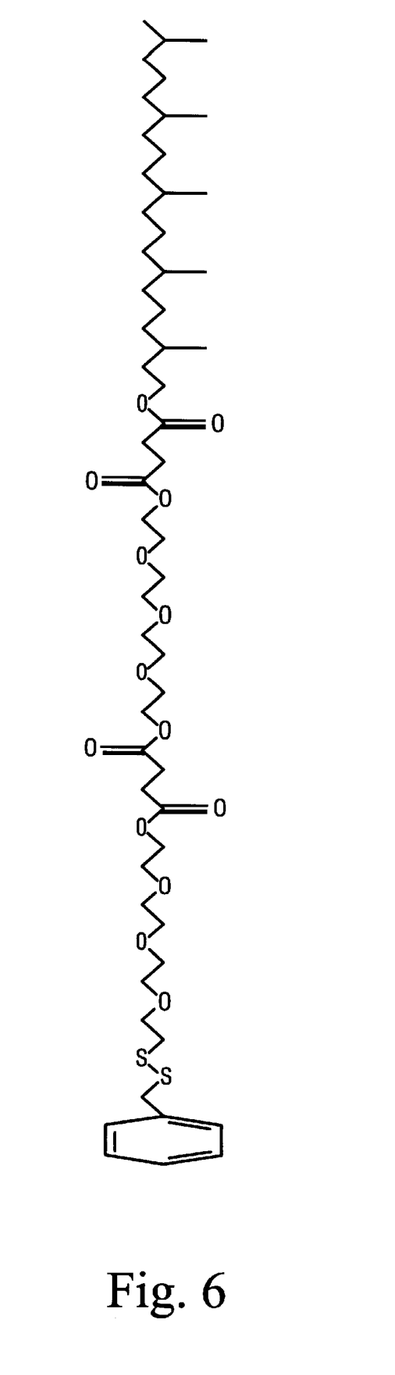
FIG. 6 is Lipid A'

1st layer: 9.3 nM Linker Gramicidin B (FIG. 3) 1.1 μM Membrane Spanner Lipid D (FIG. 4) 37 μM MAAD (FIG. 5) 75 μM Linker Lipid A (FIG. 6)

Figure 7:
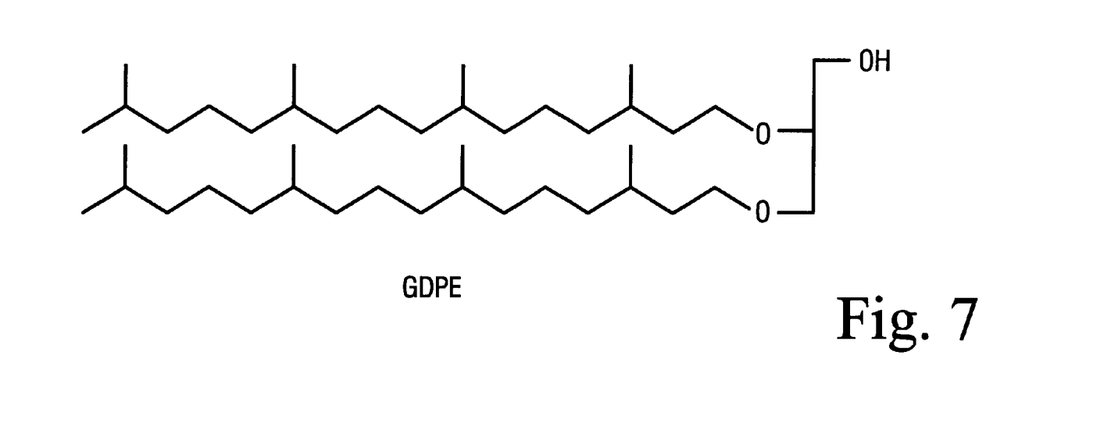
FIG. 7 is DPE-PC.
Figure 8:
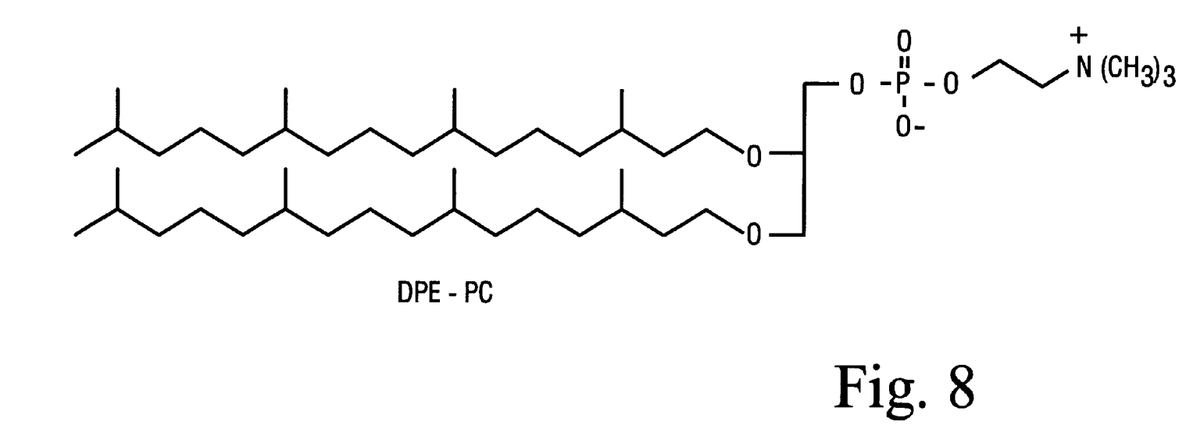
FIG. 8 is GDPE.
Figure 9:
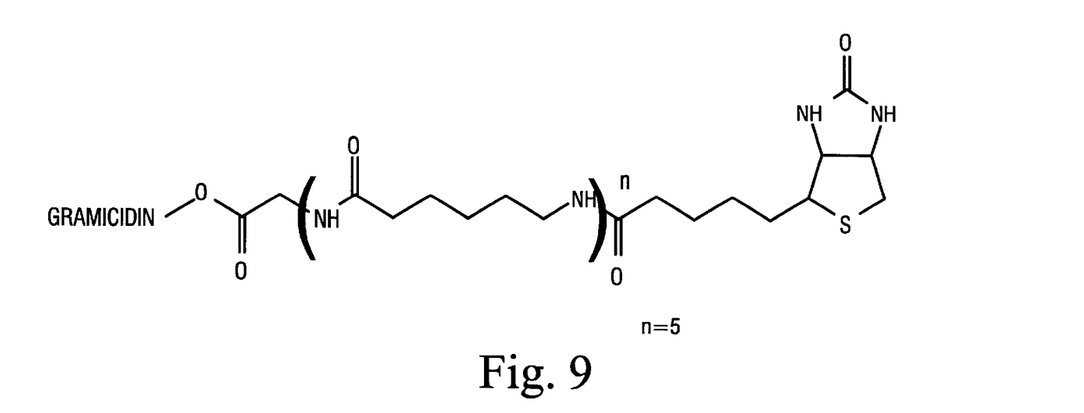
FIG. 9 is biotinylated gramicidin E.

2nd layer: 10 mM (DPE-PC (FIG. 7):GDPE (FIG. 8)=7:3): Biotinylated Gramicidin E (FIG. 9)=66,677:1 in ethanol.

Electrodes with freshly evaporated gold (1000 Å) on a chrome adhesion layer (200 Å on glass microscope slides) were dipped into an ethanolic solution of the first layer components for 1 hour at room temperature, rinsed with ethanol, then stored at 4° C. under ethanol until used for impedance measurements. The slide was clamped into a block containing teflon coated wells which defined the area of the working electrode as approximately 16 mm².

Figure 10:
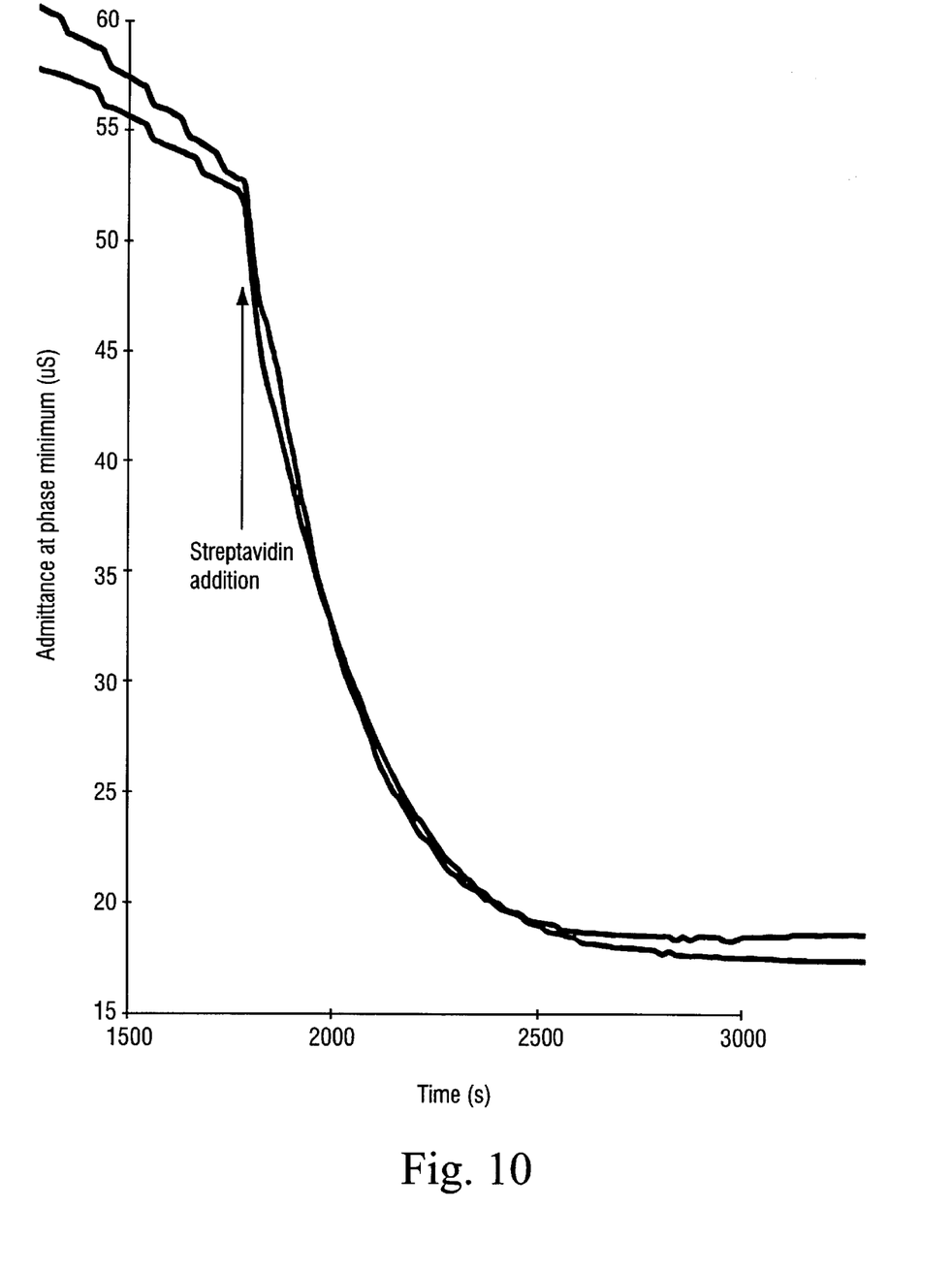
FIG. 10 is a plot of admittance at minimum phase with respect to binding of streptavidin to biotinylated gramicidin E.

5 μL of the second layer was added to the working electrode before addition of a 150 μL volume of phosphate buffered saline (6.26 mM NaCl, 59.4 mM $NaH_2PO_4$. $2H_2O$, 2.53 mM $Na_2HPO_4$. $12H_2O$, 50 mM EDTA at pH 7.4; PBS). The electrode was then washed 4 times using PBS and raised to 60° C. over a 30 minute period. Streptavidin was added to the sensor wells (5 μL 0.01 mg/ml in PBS) and incubated. The binding of streptavidin to the biotinylated gramicidin E gave a decrease in the admittance at minimum phase (FIG. 10). After 15 minutes the excess streptavidin was washed out with PBS. Wells with no added streptavidin were run as controls.

Figure 11:
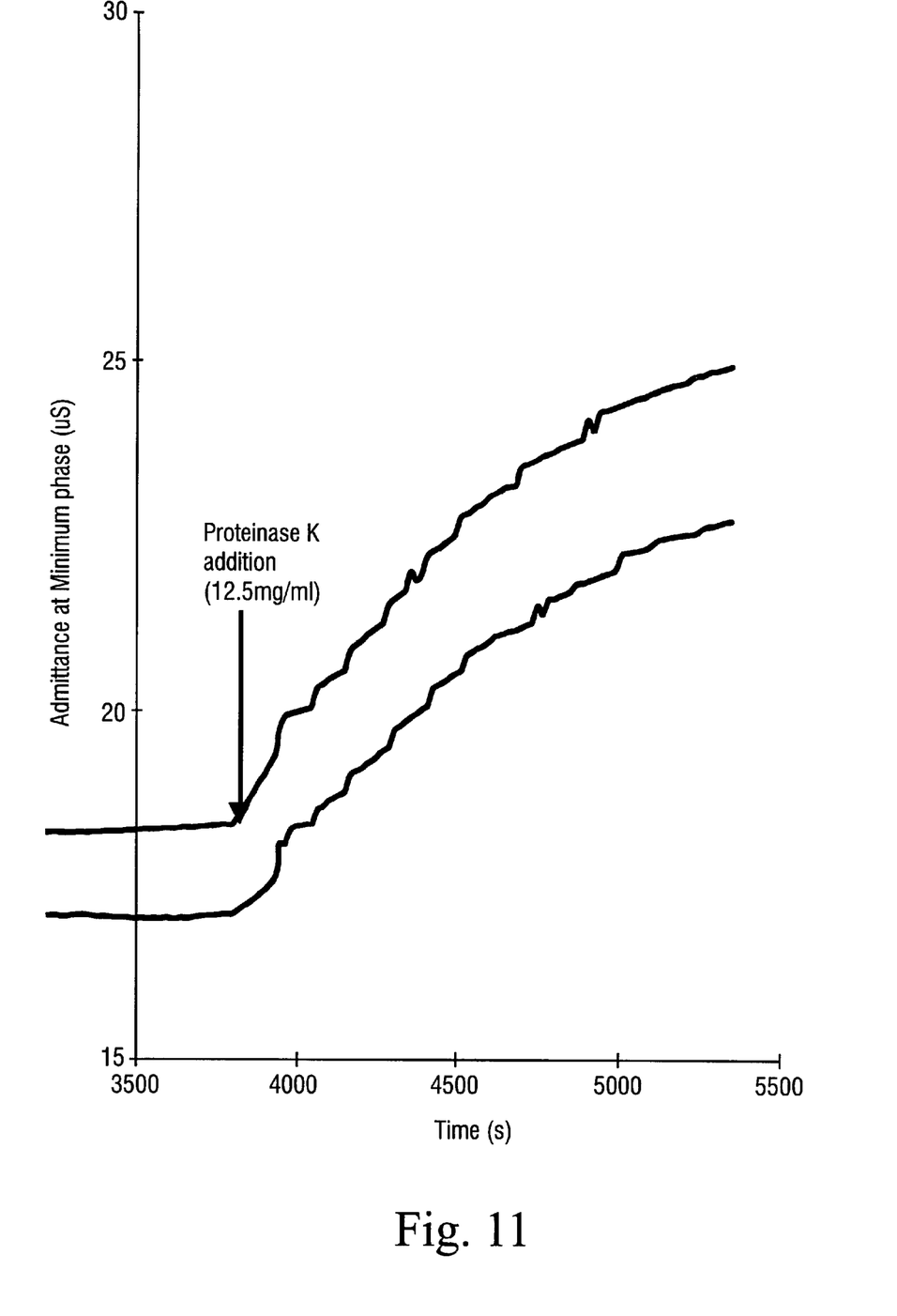
FIG. 11 is a plot of admittance at minimum phase with respect to sensor membranes to which streptavidin was bound.

Proteinase K was added to sensing and control wells to give end well concentration at 12.5 mg/ml (Boehringer Mannheim D-68298 made in PBS). Addition of Proteinase K to control wells caused no significant change in membrane admittance characteristic. Sensor membranes to which streptavidin was bound exhibited an increase in admittance at minimum phase (FIG. 11). The amount and rate of increase of admittance at minimum phase is related to the amount of proteinase K present in the test solution and therefore can be used to determine enzymatic activity in test solutions.

Example 2
Dnase 1 cleavage of DNA-bound channels

Figure 12:
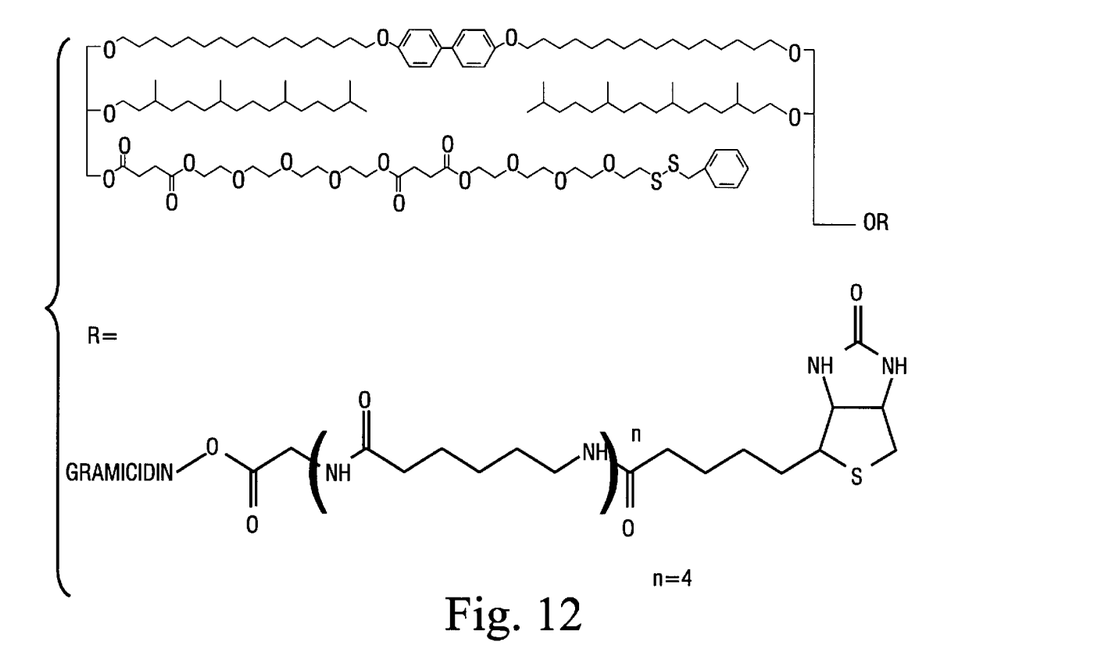
FIG. 12 is membrane spanner lipid C.

1st layer: 9.3 nM Linker Gramicidin B 1.1 μM Membrane Spanner Lipid D 27.5 nM Membrane Spanner Lipid C (FIG. 12) 37 μM MAAD 75 μM Linker Lipid A 2nd layer: 14 mM (DPE-PC:GDPE=7:3): Biotinylated Gramicidin E=50.000:1 in ethanol.

Electrodes with freshly evaporated gold (1000 Å) on a chrome adhesion layer (200 Å) on glass microscope slides) were dipped into an ethanolic solution of the first layer components for 1 hour at room temperature. rinsed with ethanol. then stored at 4° C. under ethanol until used for impedance measurements. The slide was clamped into a block containing teflon coated wells which defined the area of the working electrode as approximately 16 mm².

Figure 13:
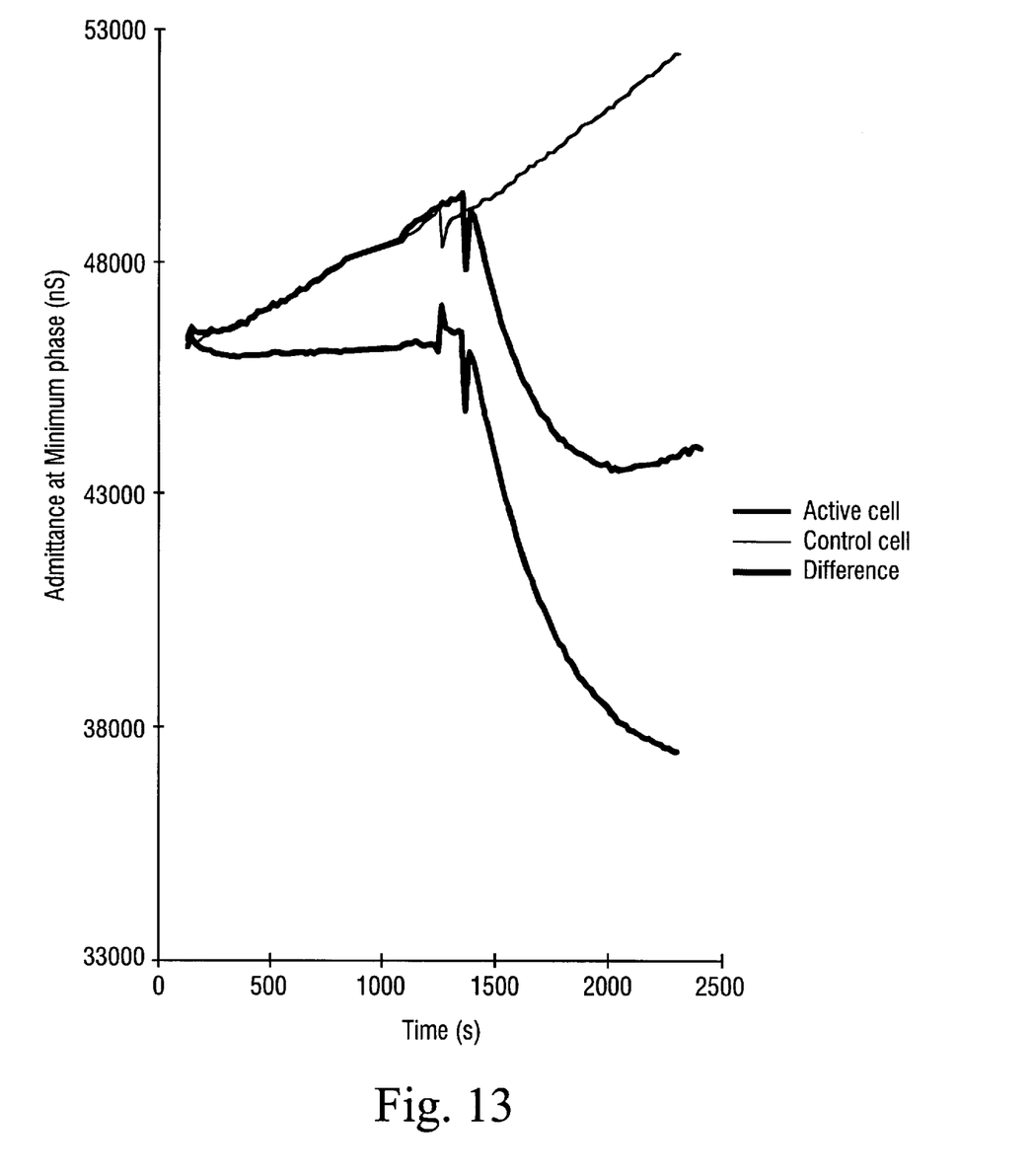
FIG. 13 is a plot of admittance at minimum phase with respect to binding of DNA target I to sensor wells.
Figure 14:
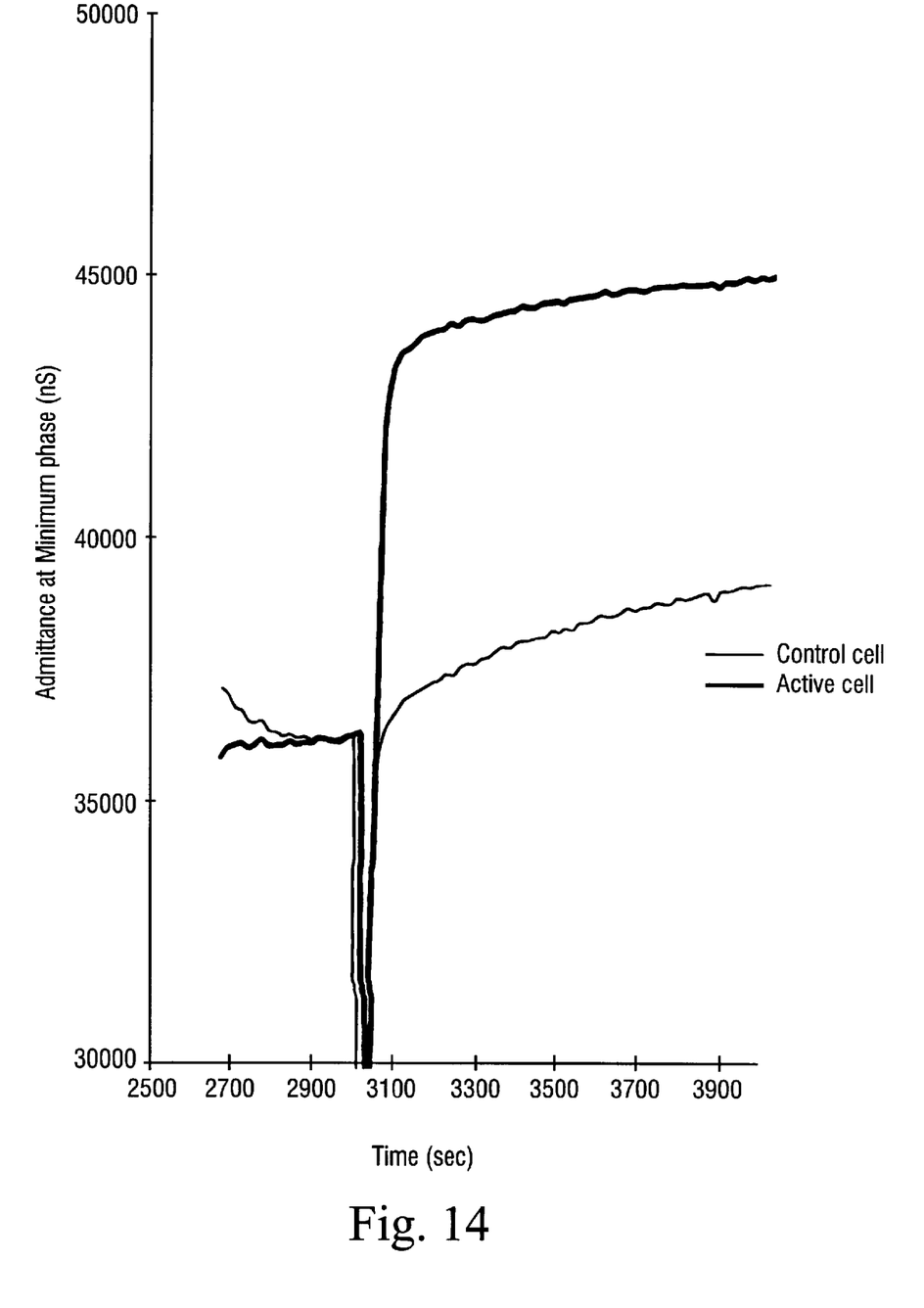
FIG. 14 is a plot of admittance at minimum phase with respect to addition of DNase 1 for sensor wells.

5 μL of the second layer was added to the working electrode before addition of a 180 μL volume of phosphate buffered saline (10 mM $NaH_2PO_4$, 1 mM $KH_2PO_4$, 137 mM NaCl, 2.7 mM KCl: PBS). The electrode was washed 4 times using PBS. These steps were carried out at room temperature. All the subsequent steps were carried out at 30° C. Streptavidin was added to all the wells (5 μL 0.01 mg/ml in PBS) and allowed to react with biotinylated gramicidin E for 10–15 minutes before washing out excess unbound streptavidin with PBS, 5 μL of a 1:1 mixture of DNA probe F (200 nM): DNA probe G (200 nM in PBS) was added to the sensor wells. A DNA non-specific binding probe H (5 μL 400 nM in PBS) was added to control wells. Binding probe H is non-complementary to the target DNA of interest and hence target DNA should not bind. The probes were allowed to react with streptavidin for 10–15 minutes then excess unbound probes were washed out with PBS. 100 μL of DNA target I (10 nM) in PBS was added to each well. The binding of DNA target I to the sensor wells gave a decrease in the admittance at minimum phase, but no significant change in membrane admittance in control wells (FIG. 13). After 15 minutes unbound DNA target I was washed out with DNase 1 activation buffer. DNase 1 activation buffer consists of 50 nM Tris. HCl, pH 7.6. 50 nM NaCl, 10 nM MgCl$_2$, 10 nM MnCl$_2$, 0.2 mg/mL BSA. DNase 1 was added (2 μL 1 mg/mL in a 50% w/v glycerol solution of 20 mM Tris.HCl, pH 7.6. 1 mM MgCl$_2$) to sensor and control wells. Addition of DNase 1 gave an increase in admittance at minimum phase for sensor wells. but no significant change for control wells (FIG. 14). The amount and rate of increase of admittance at minimum phase is related to the amount of DNase 1 present in the test solution and therefore can be used to determine enzymatic activity in test solutions.

DNA probe F:
  5'biotinylated listeria probe DNA with a 31-atom phosphoramidite linker group between the biotin and DNA.
  5'-bio-L-M-ATAGTTTTATGGGATTAGC-3'

DNA probe G:
  5'biotinylated cholera toxin probe DNA with a 13-atom phosphoramidite linker group between the biotin and DNA.
  5'-bio-L-CTCCGGAGCATAGAGCTTGGAGG-3'

DNA non-specific binding probe H:
  5'biotinvlated 15-mer oligonucleotide with a 31-atom phosphoramidite linker group between the biotin and DNA, which is non-complementary to all parts of the target DNA sequence.
  5'-bio-L-M-ATTGCTACGTATACG-3'

DNA target I:
  52 base DNA sequence containing the 19-base listeria sequence, a 10 base 'spacer' and the 23 base cholera toxin sequence.
  5'-GCTAATCCCATAAAACTATGCATGCATAT CCTCCAAGCTCTATGCTCCGGAG-3' where:

bio = biotin

L =

M =

It will be appreciated by persons skilled in the art that numerous variations and/or modifications may be made to the invention as shown in the specific embodiments without departing from the spirit or scope of the invention as broadly described. The present embodiments are. therefore. to be considered in all respects as illustrative and not restrictive.

What is claimed is:

1. A biosensor for use in detecting the presence of an enzyme or enzymes in a sample, the biosensor comprising a membrane and means for determining the impedance of the membrane positioned relative to the membrane such that the impedance of the membrane may be determined, the membrane having ionophores therein to which are attached linkers, the linkers being cleavable by the enzyme or enzymes to be detected, the cleavage of the linker causing a change in the ability of ions to pass through the membrane via the ionophores.

2. A biosensor as claimed in claim 1 in which the linker is attached to the membrane such that the ionophore is prevented from diffusing laterally within the membrane.

3. A biosensor as claimed in claim 2 in which the linker is attached to membrane spanning components provided in the membrane.

4. A biosensor as claimed in claim 3 in which the linker is attached to the membrane spanning component via a ligand binding pair.

5. A biosensor as claimed in claim 1 in which the membrane comprises a first and second layer of a closely packed array of amphiphilic molecules, a plurality of ionophores and a plurality of membrane-spanning lipids prevented from lateral diffusion in the membrane, the ionophores comprising first and second half membrane spanning monomers, the first half membrane spanning monomers being provided in the first layer and the second half membrane spanning monomers being provided in the second layer, the first half membrane spanning monomers being prevented from lateral diffusion in the first layer, the second half membrane spanning monomers being linked to the membrane spanning lipids via the linker.

6. A biosensor as claimed in claim 1 in which the ionophores are gramicidin or analogues thereof.

7. A biosensor as claimed in claim 1 in which the enzyme to be detected is a protease.

8. A biosensor as claimed in claim 7 in which the protease is Prostate Specific Antigen.

9. A biosensor as claimed in claim 1 in which the enzyme to be detected is a nuclease.

10. A biosensor for use in detecting the presence of an enzyme in a sample, the biosensor comprising a membrane and means for determining the impedance of the membrane positioned relative to the membrane such that the impedance of the membrane may be determined, the membrane having a plurality of ionophores and a plurality of membrane-spanning components therein, the membrane-spanning components having attached thereto linker molecules to which are connected the ionophores, the linker molecules being cleavable by the enzyme to be detected, the cleavage of the linker molecules causing a change in the ability of ions to pass through the membrane via the ionophores.

11. A biosensor as claimed in claim 10 in which the membrane comprises a first and second layer of a closely packed array of amphiphilic molecules and the membrane-spanning components are prevented from lateral diffusion in the membrane.

12. A biosensor as claimed in claim 10 in which the ionophores comprise first and second half membrane spanning monomers, the first half membrane spanning monomers being provided in the first layer and the second half membrane spanning monomers being provided in the second layer with the first half membrane spanning monomers being prevented from lateral diffusion in the first layer.

13. A biosensor as claimed in claim 10 in which the ionophores are gramicidin or analogues thereof.

14. A biosensor as claimed in claim 10 in which the enzyme to be detected is a protease.

15. A biosensor as claimed in claim 14 in which the protease is Prostate Specific Antigen.

16. A biosensor as claimed in claim 10 in which the enzyme to be detected is a protease.

17. A biosensor for the detection of enzymes comprising first and second zones, means to allow addition of a sample suspected to contain a protease to the first zone, the first zone containing a probe linked to a carrier via a linker cleavable by the enzyme and means to allow passage of unlinked probe from the first zone to the second zone; the second zone including a membrane the impedance of which is dependent on the presence or absence of the probe and means to measure the impedance of the membrane positioned relative to the membrane such that the impedance of the membrane may be determined.

18. A biosensor as claimed in claim 17 in which the membrane comprises a first and second layer of a closely packed array of amphiphilic molecules and a plurality of ionophores comprising first and second half membrane spanning monomers, the first half membrane spanning monomers being provided in the first layer and the second half membrane spanning monomers being provided in the second layer, the second half membrane spanning monomers being capable of lateral diffusion within the second layer independent of the first half membrane spanning monomers, the first half membrane spanning monomers being prevented from lateral diffusion in the first layer, and a ligand provided on at least the second half membrane spanning monomers, said ligand being reactive with the probe or a portion thereof, the binding of the probe to the ligand causing a change in the relationship between the first half membrane spanning monomers and the second half membrane spanning monomers such that the flow of ions across the membrane via the ionophores is allowed or prevented.

19. A biosensor as claimed in claim 17 in which the enzymes to be detected are proteases.

20. A biosensor as claimed in claim 19 in which the protease is Prostate Specific Antigen.

21. A biosensor as claimed in claim 17 in which the enzyme to be detected is a nuclease.

22. A biosensor as claimed in claim 17 in which the half membrane spanning monomers are gramicidin or analogues thereof.

23. A biosensor as claimed in claim 17 in which the probe includes an ionphore.

24. A method of detecting the presence of an enzyme in a sample comprising adding the sample to the biosensor as claimed in claim 1 and measuring the change in impedance of the membrane.

25. A method as claimed in claim 24 in which the enzymes to be detected are proteases.

26. A method as claimed in claim 25 in which the protease is Prostate Specific Antigen.

27. A biosensor for use in detecting the presence of an enzyme or enzymes in a sample, the biosensor comprising a membrane and a detector positioned relative to the membrane for determining the impedance of the membrane, the membrane having ionophores therein to which are attached linkers, the linkers being cleavable by the enzyme or enzymes to be detected, the cleavage of a linker causing a change in the ability of ions to pass through the membrane via the ionophores.

* * * * *